United States Patent
Weiss et al.

(10) Patent No.: US 8,357,510 B2
(45) Date of Patent: Jan. 22, 2013

(54) PROCESS FOR OBTAINING LUTEIN FROM ALGAE

(75) Inventors: Albrecht Weiss, Langenfeld (DE);
Wilhelm Johannisbauer, Erkrath (DE);
Bernhard Gutsche, Hilden (DE);
Baldomero F. Cordero, Bormujos Sevilla (ES); Lucia Martin, Sevilla (ES); Herminia Rodriguez, Sevilla (ES); M. Angeles Vargas, Dos-Hermanes Sevilla (ES); Irina Obraztsova, Sevilla (ES)

(73) Assignee: Cognis IP Management GmbH, Duesseldorf (DE)

( * ) Notice: Subject to any disclaimer, the term of this patent is extended or adjusted under 35 U.S.C. 154(b) by 143 days.

(21) Appl. No.: 11/651,792

(22) Filed: Jan. 10, 2007

(65) Prior Publication Data

US 2007/0196893 A1    Aug. 23, 2007

(30) Foreign Application Priority Data

Jan. 12, 2006 (EP) .................................. 06000599

(51) Int. Cl.
*C12P 23/00* (2006.01)
(52) U.S. Cl. .......................... 435/67; 585/351
(58) Field of Classification Search .................. None
See application file for complete search history.

(56) References Cited

U.S. PATENT DOCUMENTS

| | | | |
|---|---|---|---|
| 3,280,502 A | 10/1966 | Farrow et al. | |
| 4,391,291 A | 7/1983 | Hume | |
| 5,827,539 A * | 10/1998 | Gellenbeck | 424/489 |
| 6,261,598 B1 | 7/2001 | Runge et al. | |

FOREIGN PATENT DOCUMENTS

| EP | 0 251 018 | 1/1988 |
|---|---|---|
| WO | WO 89/06910 | 8/1989 |

OTHER PUBLICATIONS

Shi & Chen, Nahrung, 1999, No. 2, p. 109-113.*
Lee, Journal of applied Phycology, 2001, vol. 13-, p. 307-315.*
Garcia et al., Process Biochemistry, 2005, vol. 40, p. 297-305.*
Nelis et al., Journal of Applied Bacteriology, 1991, vol. 70, p. 181-191.*
Prasad et al., Journal of the American College of Nutrition 1999, vol. 18, No. 1, p. 13-25.*
Lee et al., Journal of Applied Phycology, 1996, vol. 8, p. 163-169.*
Sommerburg et al., Br J Ophthalmol, 1998, vol. 82, p. 907-910.*
Matsukawa et al., Journal of Applied Phycology. 2000, vol. 12, p. 263-267.*
Ishikawa et al., Journal of Applied Phycology, 2004, vol. 16, p. 385-393.*
Shi et al., "High-Yield Production of Lutein by the Green Microalga *Chlorelle potothecoldes* in Heterotrophic Fed-Batch Culture", Biotechnol. Prog., 18, 2002, pp. 723-727.
Del Campo et al., Accumulation of astaxanthin and lutein in *Chlorelle zofinglenas* (Chlorophyta), Appl.Microbiol Biotechnol, 64, 2004, pp. 848-654.
Del Campo et al., Carotenold content of chlorophycean microalgae: factors determining lutein accumulation in *Muriellopsis* sp. (Chlorophyta), Elsevier Sdence B.V., Journ.Biotechnology, 76, 2000, pp. 51-59. XP002376925.
Matsukawa et al., "Antioxidants from carbon dioxide fixing *Chlorella sorokinlana*", Journ.Applied Phycology, 12, 2000, pp. 263-267. XP002376926.
Erich Kessler, et al. Comparative Physiology and Biochemistry and Taxonomic Assignment of the *Chlorella* (Chlorophyceae) Strains of the Culture Collection of the University of Texas at Austin, J. Phycol. 28, 550-553 (1992).
Robert J. Theriault, Heterotrophic Growth and Production of Xanthophylls by *Chlorella pyrenoidosa*, Applied Microbiology, May, (1965), vol. 13. No. 5, p. 402-416.
Lang, Imke, et al., "Fatty acid profiles and their distribution patterns in microalgae: a comprehensive analysis of more than 2000 strains from the SAG culture collection", *BMC Plant Biology*, 2011, 11:124, 16 pgs.
Lin, Rong-Fong, et al., "Comparative Studies on Heterotrophic Growth of Thermophilic *Chlorella*", *J. National Taiwan Normal University*, 2002, 47(1):31-40, 9 pgs.
Roldán, M, et al., "Does Green Light Influence the Fluorescence Properties and Structure of Phototrophic Biofilms?", *Appl. Environ. Microbiol. 2006*, 72(4):3026-3031, 6 pgs.

* cited by examiner

*Primary Examiner* — Kade Ariani
(74) *Attorney, Agent, or Firm* — Diehl Servilla LLC

(57) ABSTRACT

A process of obtaining lutein in a high yield from green algae is described. Lutein and lutein-enriched products obtained by the process, which are suitable for use as dietary supplements and/or food additives, or cosmetic or pharmaceutical raw materials, are also described.

14 Claims, No Drawings

PROCESS FOR OBTAINING LUTEIN FROM ALGAE

CROSS-REFERENCE TO RELATED APPLICATIONS

This application claims priority under 35 USC Section 119 of European patent application, EP06000599 filed Jan. 12, 2006, which is incorporated herein in its entirety.

FIELD OF THE INVENTION

The present invention relates to a process for obtaining lutein from green algae for the production of lutein and lutein-enriched products.

BACKGROUND OF THE INVENTION

Lutein, together with zeaxanthin, is an essential component of the macular pigment in the retina of the eye. A low level of intake of this particular carotenoid increases the risk of age-related macular degeneration (AMD) and cataracts, which are the leading causes of visual impairment and acquired blindness, and are key quality of life issues among millions of ageing people. One of the first large-scale studies on carotenoids is the Eye Disease Case Control Study, in which diet was compared to the risk of developing AMD. Results found a significantly lower risk of developing the eye disease in people showing high amounts of lutein and zeaxanthin in their blood. Also, the people who followed a diet with the highest amounts of lutein and zeaxanthin developed a significantly lower risk of AMD than those whose diet contained the lowest amount (as low as 1.2 mg per day). Dietary studies confirmed the association between frequent consumption of spinach or collard greens, which are particular good sources of lutein and zeaxanthin and of lower AMD risk. Similar results were found in a recent analysis of a US dietary study called the Third National Health and Nutrition Examination Survey or NHANES III. This analysis also showed that consuming lutein and zeaxanthin was associated with a reduced risk of developing AMD.

Lutein (3,3'-dihydroxy-β,ε-carotene) represents an oxygenated carotenoid or xanthophyll. The conjugated double bond system determines its yellow color and is responsible for the biological activity.

mg/dry weight), however it grows slowly (doubling time 17.3 h) and therefore its productivity is poor (Appl. Microbiol. Biotechnol. 64, 848-654 (2004)). *Muriellopsis* was grown autotrophically in batch culture showing a maximal content of lutein in the cultures of 35 mg $l^{-1}$ and an estimated productivity of 32.6 mg l–1 h–1 under optimized environmental and nutritional conditions of growth (J. Biotechnol. 76, 51-59 (2000)). In addition, several patents claim the use of various strains of *Chlorella* for the production of lutein, however, their productivity is too low for an industrial production under economic acceptable conditions (U.S. Pat. No. 4,391,291; EP 0251018 A1). Currently, lutein is produced from plants, mainly marigold flowers, which have large requirements of land showing rather low content in lutein.

The complex problem underlying the present invention has therefore been to develop a process which provides lutein from natural sources in higher yields compared to the state of the art, more particularly from algae showing simultaneously:
- a specific growth rate μ at medium light conditions of at least 0.05 $h^{-1}$ (measured under phototropic conditions using inorganic media);
- a production of biomass per volume at medium light radiation and under phototropic conditions using inorganic media of at least 8 g dry biomass/l;
- a lutein/zeaxanthin ratio of more than 5;
- a factor obtained by multiplication of growth rate and lutein volumetric productivity of at least 0.02 mg $l^{-1}h^{-2}$;
- a chlorophyll A /lutein ratio of less than 10, and
- a volumetric lutein productivity of at least 0.2 mg $l^{-1}h^{-1}$.

In addition, the starting material should be easy to cultivate and to harvest, so that it is possible to carry out the reaction in a photo-bioreactor. Finally, the sources should be free of any harmful toxins or be cultivated under such non-toxin-producing conditions to avoid harmful toxin formation, and be resistant against contamination.

BRIEF DESCRIPTION OF THE INVENTION

The present invention is directed to a process for obtaining lutein or a lutein-enriched product, which process provides for:
(a) cultivating a green algae selected from the group consisting of *Chlorella sorokiniana* (SAG 211-32), *Neospongiococcum gelatinosum* (SAG 64.80) and *Chlorococcum citriforme* (SAG 62.80) under cultivating conditions suitable for producing lutein;
(b) harvesting the cultivated algae containing lutein; and
(c) obtaining the lutein from the harvested algae containing lutein.

Surprisingly, it had been found that green algae, described above for use in the process of the invention, produce the desired lutein in a significantly higher amount, as compared with any other known algae reported in the state of the art.

The above-described green algae, particularly *Chlorella sorokiniana*, exhibit a number of additional advantages com-

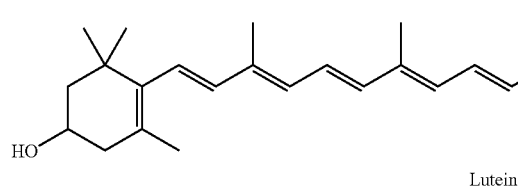
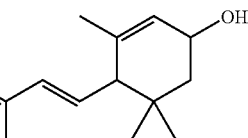

Lutein

The physiological properties of lutein and particularly its function as an antioxidant are due to its potential to inactivate singlet oxygen and to quench active radicals. Up to today, lutein is mainly produced synthetically since the content of this carotenoid in natural sources is considered to be rather low for any industrial production under economic conditions. In the case of fed-batch heterotrophic cultures of *Chlorella protothecoides*, an average lutein productivity of 22.7 m $l^{-1}$ $d^{-1}$ in a 3.7-L fermenter was obtained. (Biotechnol. Prog., 18, 723-727(2002)). *Chlorella zofingiensis* grown autotrophically in batch culture exhibited lutein contents of 20 mg/l (=4 pared to other algae: quick growth times (doubling time of 3 hrs.), no cell clumping; and are facile to handle, so that they are suitable for cultivation, especially in tubular photo-bioreactors. The algae useful in the invention grow auto- or mixotrophically in a very simple and cheap mineral medium, and are resistant with respect to contamination.

Another aspect of the invention is a lutein or lutein-enriched product obtained by way of the invention having a lutein/zeaxanthin ratio of greater than about 5 and a chlorophyll A/lutein ratio of less than about 10.

The lutein or lutein-enriched product is especially suitable for use as a dietary supplement or food additive, or as a cosmetic or pharmaceutical raw material.

DETAILED DESCRIPTION OF THE INVENTION

Other than in the operating examples, all numbers expressing quantities of ingredients or reaction conditions of the process are to be understood as being modified in all instances by the term "about."

Green Algae

Among the three strains cited above, Chlorella sorokiniana (SAG 211-32) is preferred since it does not only exhibit a high productivity with respect to lutein, but also shows the best resistance against pollutants, and exhibits the fastest growth rate, without cell clumping. Nevertheless, it shall be understood that the present invention is not limited to these wild forms, but also encompasses any mutants of these strains including forms obtained by genetic modification or engineering.

Cultivation Conditions

Many culture conditions and culture media are known for small-scale stock cultures and large-scale cultures of algae cells. However, for the purposes of the present invention, it was found that the optimal culture conditions and media are actually the relatively simple culture conditions and media described herein below, these therefore being the preferred ones in accordance with the invention. For example, temperature is a factor for the growth of algae. It has been found that very favorable conditions are achieved at between 20 and 40° C. with a temperature of about 30° C. being particularly suitable.

In a further embodiment of the invention, the algae are grown mixotrophically (with additional nutrients to enhance cell growth), more particularly, Amon medium has been found to support the growth in an optimal manner, preferably in combination with nitrates in amounts of 10 to 60 mM, preferably about 40 mM. The growth rate can also be increased by the addition of salts of acetic acid, in particular sodium acetate, in amounts of from about 20 to 60 mM, preferably about 40 mM.

Irradiation of the cells during cultivation can also be carried out. As far as screening and pilot plant tests are concerned, mercury halide lamps are typically used and cultivation is carried out under a light irradiation of from about 200 to 1,500 $\mu Em^{-2}s^{-1}$, and preferably about 700 $\mu Em^{-2}s^{-1}$. For production, natural light conditions are particularly suitable.

In a further embodiment of the present invention, the cells are cultivated in a photo-bioreactor, preferably a tubular or a panel photo-bioreactor, having the advantage of a very large surface area with respect to its volume for optimal large-scale production of algae cells in their growth phase. Usually, such bioreactor modules have a volume in the range from 100 to 35,000 liters; depending on the scale of production that is desired. Components containing commercially available tubes made of PVC, acrylic (Plexiglas™), polycarbonate or glass, having an inner diameter of about 3 to 5 cm, are suitable for use. In operation, the culture cells are circulated through the device in tap water to which $CO_2$ is added, using a pump. The green cultures from the liquid stock cultures (or inoccula) are inoculated into the photo-bioreactor, in which the algae are sparged with a $CO_2$ containing gas, such as a mixture of $CO_2$ in air or $CO_2$ as the main gas component. Sparging and pumping also serve to prevent clumping of the cells. For production scale in a tubular photo-bioreactor, 90 to 100% pure $CO_2$ can be utilized; also inexpensive $CO_2$ from industrial plants (e.g. from a quick lime process) is especially suitable.

The initial cell concentration in the photo-bioreactor during the process of cultivation is preferably adjusted from about 0.1 to $0.3 \times 10^6$ cells/ml at cell concentrations (dry mass) between 0.1-0.4 g dry biomass/l, by dilution with fresh modified cultivation medium. The light intensity is usually maintained in the range of between about 200 and 1,500 $\mu Em^{-2}s^{-1}$ as provided by mercury halide lamps or as natural light. It has been found advantageous to maintain the temperature in the photo-bioreactor in the range between 25 and 28° C. By using a glass house as an indoor cultivation room, temperatures can be maintained below 32° C., as a non-limiting example, in central and northern Europe in summer time. In addition, the tubular photo-bioreactor and the indoor placement have the advantage of clean, long term and controlled operation, and if the photo-bioreactor is made of glass tubes instead of plastic, extensive maintenance or revamping in order to operate for a long time is not necessary. Further, the culture conditions are extremely inexpensive as the cells are grown in a cheap mineral medium of tap water with the addition of carbon dioxide as, essentially, the major nutrient source.

It should be noted that the carotenoid yields can be increased further by stress factors (light irradiation, chemical stress, salts, pH, temperature, oxidative stress).

Harvesting and Recovery of Lutein

In order to obtain lutein or a lutein-enriched product from the cultivated algae cells, many procedures have been described, for example, the procedures in WO 89/006910. While these procedures may be employed in accordance with the present invention, the preferred procedure is that of centrifugation, or sedimentation or filtration under vacuum to concentrate the cells, and drying of the concentrated cells. The dried cell mass is then preferably stored at low temperatures (e.g., −20° C. or lower) under oxygen-free conditions, e.g., by vacuum packing or, preferably, by introduction into plastic bags together with nitrogen ($N_2$) to remove the oxygen.

In a further embodiment of the invention, the process comprises the following additional steps:
 (i) harvesting the cells cultivated in step (b) by collecting said cells to form a concentrated suspension,
 (ii) optionally adding antioxidants and emulsifiers to said suspension, and optionally
 (iii) disrupting the collected cells, and drying them to obtain a lutein or a lutein-enriched product.

Generally, the collection and concentration of the cells is carried out by centrifugation, or sedimentation, or filtration under vacuum, and the drying of the cells is carried out by lyophilization, combined drying and grinding (air-vortex-mill), or spray drying.

More particularly, while each cultivation cycle optimally lasts about four to six days, the following harvesting procedure is performed based on the fact that algae cells readily sediment once collected from the photo-bioreactor. Thus, the cell biomass from the photo-bioreactor is collected into a standard large volume funnel, e.g. an Imhoff funnel, and left to stand for a few hours (about 3-5 hours) to facilitate sedimentation of the cells. It was found that approximately 30% b.w. of the total volume of biomass from the bioreactor represented the cell sediment, while the remaining approximately 70% b.w. of the total collected volume represented the tap water used in the cultivation. This tap water can thus be easily collected and used for a new bioreactor inoculation and cultivation procedure (i.e., the originally used tap water is almost completely recyclable). The above precipitated and concentrated cell culture is then collected from the funnel and subjected to centrifugation or vacuum filtration to further concentrate the cells. Routinely, a biomass yield of about 40% b.w. solids is obtained following the centrifugation step, or about 30% b.w. solids following vacuum filtration. Here, too, the approximately 60% b.w. of the total volume subjected to centrifugation, or approximately 70% b.w. of the total volume subjected to vacuum filtration, being the supernatant volume, can also be collected and used for another round of the cultivation procedure, this supernatant being primarily the original tap water used in the procedure.

The concentrated cell slurry obtained from the above centrifugation step is then homogenized and stabilized by adding antioxidants and then dried, preferably by lyophilization, although spray drying can also be utilized. Suitable antioxidants can be selected from ethoxyquin, butylated hydroxyanisole, butylated hydroxytoluene (BHT), tocopherols, di-tert-butyl-paracresol and propyl gallate. The preferred antioxidant is a natural tocopherol product containing 30% b.w. of alpha tocopherol. Usually, the amount of antioxidant added in the grinding procedure can range from about 0.05 to 5% (w/w) of the amount of dry powder. The powders are packed into a plastic bag pre-filled with nitrogen gas to remove oxygen (which causes pigment oxidation, i.e. degradation of the active) and are then stored at −20° C. prior, e.g., to processing to prepare the food additive.

The final stage of producing a lutein or a lutein-enriched product in the form of small particles easily digested by humans or animals may also be carried out in a number of ways as previously described in the art. Thus, lutein and other algae components are processed to assure a high bioavailability. The preferred procedure involves the use of a standard ball mill in which the biomass slurry is disintegrated as a suspension in water in the presence of any suitable antioxidant to prevent oxidation of the lutein. After drying, this yields a powder-like product of small particle size.

The powder thus obtained may then be utilized directly or in a mixture with other ingredients as an additive to fish meal for coloration or in food applications like dietary supplements. In another process, the lutein can be concentrated by an extraction process including extraction with supercritical solvents, which lutein is suitable for use in the formulation of food supplements or pharmaceutical products.

Industrial Application

According to the teaching of the present invention, certain green algae have been found to exhibit a surprisingly high productivity for the production of lutein under the process conditions described herein. Another aspect of the present invention is therefore directed to the use of green algae selected from the group of strains of *Chlorella sorokiniana* (SAG 211-32), *Neospongiococcum gelatinosum* (SAG 64.80) and *Chlorococcum citriforme* (SAG 62.80), either in their wild forms or in the form of any mutant, including those forms obtained from by genetic modification or engineering for the production of lutein or lutein-enriched products.

Another embodiment of the present invention relates to the use of lutein or lutein-enriched products, including the lutein enriched biomass (as directly obtained from the cultivation) as a food or feed additive, or a cosmetic or pharmaceutical raw material.

The following examples are illustrative of the invention and should not be construed in any manner whatsoever as limiting the scope of the invention.

EXAMPLES

Lutein Analysis

For the analysis of lutein, the pigments were extracted with methanol at 70° C., centrifuged, the supernatant evaporated under $N_2$ on ice and the pellet re-suspended in methanol, centrifuged and analyzed by HPLC using a Waters Spherisorb S5 ODS1 4.6×250 mm cartridge column. The pigments were detected by using a photodiode-array detector.

Cell Growth Conditions

Stock cultures of microalgae were grown photoautotrophically in batch culture, in 100 ml of Arnon culture medium (Arnon medium, modified to contain 4 mM $K_2HPO_4$ and 20 mM $NaNO_3$; Arnon et al., 1974) in conical flasks of 200 ml capacity and illuminated with fluorescents lamps at 92 µE $m^{-2}s^{-1}$. Culture temperature was 25° C. The screening of the strains for the production of lutein was performed under the following conditions:

Photoautotrophic batch cultures in Roux Flasks (750 ml) were started with cells at the exponential phase from the stock cultures at a cell density of $0.1$-$0.3 \times 10^6$ cells $ml^{-1}$;

Irradiance: Continuous, 460 µE $m^{-2}$ $s^{-1}$ (mercury halide lamps);

Temperature: 28° C.;

Bubbling: The cultures were bubbled with air supplemented with 1%(v/v) $CO_2$;

Culture medium: The same as in the case of stock culture;

Several parameters were analyzed in the different microalgae, as cell density, dry weight, carotenoids, pH, cell morphology and the specific growth rate ($\mu$). Growth was followed by determining the cell number, by using a Coulter Counter or by dry weight (g $l^{-1}$). For dry weight determinations, 5 ml aliquots were filtered through previously weighted Whatman filters (1.2 µm diameter), washed twice with distilled water and dried at 80° C. for 24 h. Lutein volumetric productivity (LVP) was calculated by multiplying the maximum specific growth rate ($\mu$) and the maximal lutein concentration at the exponential phase (MLEP). For mixotrophic growth, cultures were supplemented with 5 to 60 mM sodium acetate and for the nitrate optimization the media were supplemented with 10 to 40 mM sodium nitrate. For the optimization of irradiance, light irradiances from 92 µE $m^{-2}s^{-1}$ to 1,500 µE $m^{-2}s^{-1}$ were assayed. Temperature ranged from 22° C. to 40° C. in the experiment for temperature optimization.

Selection of Green Micro-Algae Strains

The following Tables 1 and 2 show a comparison of different green microalgae strains with respect to the productivity for lutein (P) and the factor "specific growth rate" multiplied with "lutein productivity". As outlined above, the algae were cultivated in Amon medium +20 mM $NO_3^-$ at 28° C., the irradiance was 100 $Wm^{-2}$ (460 µE $m^{-2}s^{-1}$). In general, green microalgae show high content in lutein and low content in zeaxanthin. *Chlorella sorokiniana* (SAG 211-32), *Chlorococcum citriforme* (SAG 62.80) and *Neospongiococcum gelatinosum* (SAG 64.80) exhibited the highest specific growth rates ($\mu$), from 0.13 $h^{-1}$ (*Chlorococcum citriforme*) to 0.17 $h^{-1}$ (*Chlorella sorokiniana*). In particular, *Chlorella sorokiniana* and *Neospongiococcum gelatinosum* showed the highest lutein production (24.0-25.2 mg $l^{-1}$ $day^{-1}$).

TABLE 1

Productivity of green microalgae for lutein

| Strains | μ [h$^{-1}$] | MCD [cells l$^{-1}$] | MBV [g l$^{-1}$] | MVLC [mg l$^{-1}$] | MLC [mg g$^{-1}$DW] |
|---|---|---|---|---|---|
| Chlorella sorokiniana SAG 211-32 | 0.17 | 1.5 10$^{11}$ | 16.5 | 33.3 | 3.4 |
| Neospongiococcus gelatinosum SAG 64.80 | 0.15 | 2.8 10$^{10}$ | 9.0 | 41.5 | 7.2 |
| Chlorococcum citriforme SAG 62.80 | 0.13 | 6.7 10$^9$ | 8.1 | 60.9 | 7.6 |
| Chlorella fusca SAG 211-8b | 0.05 | 2.0 10$^{11}$ | 16.4 | 34.0 | 2.5 |
| Scenedesmus armatus UTEX 2533 | 0.07 | 5.4 10$^{10}$ | 9.0 | 27.6 | 3.9 |
| Scenedesmus vacuolatus SAG 211-15 | 0.07 | 3.6 10$^{11}$ | 14.0 | 40.5 | 3.0 |
| Muriellopsis sp. | 0.05 | 2.2 10$^{11}$ | 13.0 | 40.0 | 3.1 |
| Monoraphidium braunii SAG 202.7d | 0.04 | 2.0 10$^{11}$ | 9.0 | 32.6 | 3.6 |
| Chlamydomonas reinhardtii CC621(-) | 0.08 | 3.0 10$^{10}$ | 2.0 | 5.3 | |
| Scenedesmus obliquus UTEX 393 | 0.07 | 7.4 10$^{10}$ | 10.0 | 15.3 | 2.8 |
| Chlorella zofingiensis SAG 211-14 | 0.05 | 7.0 10$^{10}$ | 8.8 | 23.1 | 2.6 |
| Chlorella luteoviridis UTEX 258 | 0.10 | 2.3 10$^{10}$ | 1.8 | 2.0 | 1.9 |

MCD = Maximal Cell density;
MBV = Maximal biomass per Volume;
MVLC = Maximal Volumetric Lutein Concentration;
MLC = Maximal Lutein Concentration;
DW = Dry weight

TABLE 2

Productivity of green microalgae for lutein (II)

| Strains | LVP [mg l$^{-1}$h$^{-1}$] | MCD MLC | MLC MZC | MLC MDW |
|---|---|---|---|---|
| Chlorella sorokiniana SAG 211-32 | 1.0 | 4.4 10$^{10}$ | 8.5 | 0.21 |
| Neospongiococcus gelatinosum SAG 64.80 | 1.05 | 3.9 10$^9$ | | 0.80 |
| Chlorococcum citriforme SAG 62.80 | 0.70 | 8.8 10$^8$ | | 0.94 |
| Chlorella fusca SAG 211-8b | 0.17 | 8.0 10$^{10}$ | 0.42 | 0.15 |
| Scenedesmus armatus UTEX 2533 | 0.35 | 1.4 10$^{10}$ | | 0.43 |
| Scenedesmus vacuolatus SAG 211-15 | 0.12 | 1.2 10$^{11}$ | 0.53 | 0.21 |
| Muriellopsis sp. | 0.19 | 7.1 10$^{10}$ | 1.6 | 0.24 |
| Monoraphidium braunii SAG 202.7d | 0.15 | 5.6 10$^{10}$ | 0.43 | 0.40 |
| Chlamydomonas reinhardtii CC621(-) | 0.18 | | | |
| Scenedesmus obliquus UTEX 393 | 0.21 | 2.6 10$^{10}$ | 3.5 | 0.28 |
| Chlorella zofingiensis SAG 211-14 | 0.10 | 2.7 10$^{10}$ | 0.87 | 0.30 |
| Chlorella luteoviridis UTEX 258 | 0.11 | 1.2 10$^{10}$ | 3.2 | 1.06 |

LVP = Lutein Volumetric Productivity;
MCD = Maximal Cell density;
MLC = Maximal Lutein Concentration;
MZC = Maximal Zeaxanthin Concentration;
MDW = Maximal Dry Weight

Kinetics of the Accumulation of Carotenoids

Table 3 presents the kinetics of accumulation of different carotenoids in the selected strain for lutein production (*Chlorella sorokiniana*, SAG 211-322). As mentioned above, lutein is the major carotenoid and, not only zeaxanthin, but also all the other carotenoids are present either in very low amounts or not detected. Lutein content in the cultures increased with time, changing from 5.9 in the exponential phase to 33.0 mg l$^{-1}$ in the stationary phase. Total carotenoids also increased with time from 7.0 to 37.1 mg l$^{-1}$.

TABLE 3

Kinetics of the accumulation of carotenoids [mgl−1]

| | Exponential phase | | Deceleration phase | | Stationary phase |
|---|---|---|---|---|---|
| Time [h] | | | | | |
| Carotenoids | 48 | 102 | 220 | 289 | 342 |
| Violaxanthin | 0.2 | 0.4 | 0.7 | 0.7 | 0.9 |
| Astaxanthin | — | — | — | — | — |
| Anteraxanthin | 0.1 | 0.2 | 0.2 | 0.2 | 0.3 |
| Lutein | 5.9 | 11.0 | 21.0 | 24.0 | 33.0 |
| Zeaxanthin | — | — | — | — | 0.4 |
| Canthaxanthin | — | 0.3 | 0.4 | 0.4 | .07 |
| β-Cryptoxanthin | — | — | — | — | — |
| Lycopene | — | — | — | — | — |
| α-Carotene | 0.2 | 0.4 | 0.1 | 0.2 | 0.2 |
| β-Carotene | 0.6 | 0.9 | 1.2 | 1.5 | 1.6 |
| Total Carotenoids | 7.0 | 13.2 | 23.6 | 27.0 | 37.1 |

Effect of Irradiance

In the following Tables 4, 5 and 6, optimized parameters with respect to irradiance, temperature and nitrate/acetate concentration for *Chlorella sorokiniana* are given. The effect of light irradiance on cell growth and lutein production was studied in the range from 92 to 1495 μE m$^{-2}$ s$^{-1}$. The specific growth rate increased with irradiance up to 690 µE m$^{-2}$s$^{-1}$ and stayed constant at higher light intensity values. In addition, maximum lutein content at the exponential phase also increased with irradiance, exhibiting an optimum at 690 µE m$^{-2}$ s$^{-1}$, which was doubled when the irradiance was increased from 460 to 690 µE m$^{-2}$s$^{-1}$ and decreasing slightly at higher irradiances. The same trend was followed by lutein production, attaining 117.6 mg l$^{-1}$ day$^{-1}$ at 690 µE m$^{-2}$s$^{-1}$

TABLE 4

Effect of light irradiance

| Irradiance | µ | MCD | MLEP | MLC [mg | Lutein Production | |
|---|---|---|---|---|---|---|
| [µE m$^{-2}$s$^{-1}$] | [h$^{-1}$] | [cells$^{-1}$] | [mg l$^{-1}$] | g$^{-1}$DW] | mg l$^{-1}$h$^{-1}$ | mg l$^{-1}$d$^{-1}$ |
| 92 | 0.30 | 1.4 10$^{11}$ | 3.2 | 5.2 | 0.96 | 23.0 |
| 230 | 0.40 | 1.3 10$^{11}$ | 5.3 | 5.0 | 2.12 | 50.9 |
| 368 | 0.43 | 1.3 10$^{11}$ | 6.4 | 5.6 | 2.75 | 66.0 |
| 460 | 0.45 | 1.5 10$^{11}$ | 4.8 | 3.3 | 2.16 | 51.8 |
| 690 | 0.49 | 1.7 10$^{11}$ | 10.0 | 4.0 | 4.90 | 117.6 |
| 920 | 0.49 | 1.3 10$^{11}$ | 7.9 | 3.7 | 3.90 | 93.6 |
| 1495 | 0.49 | 1.4 10$^{11}$ | 8.8 | 3.9 | 4.31 | 103.5 |

MLEP = Maximal Lutein Concentration at the Exponential Phase

Effect of Temperature

Table 5 shows the effect of temperature on cell growth, lutein content and lutein productivity in Chlorella sorokiniana. Specific growth rate, maximum volumetric lutein content in the exponential phase and lutein productivity increased when temperature was raised, reached a maximum at 28° C. and remained at this level even at higher temperature of 40° C.

TABLE 5

Effect of temperature

| Temperature | µ | MCD | MLEP | MLC [mg | Lutein Production | |
|---|---|---|---|---|---|---|
| [° C.] | [h$^{-1}$] | [cells$^{-1}$] | mg l$^{-1}$] | g$^{-1}$DW] | mg l$^{-1}$h$^{-1}$ | mg l$^{-1}$d$^{-1}$ |
| 22 | 0.16 | 1.2 10$^{11}$ | 5.3 | 4.2 | 0.85 | 20.4 |
| 25 | 0.17 | 1.2 10$^{11}$ | 6.5 | 4.1 | 1.10 | 26.4 |
| 28 | 0.25 | 1.3 10$^{11}$ | 7.4 | 4.3 | 1.85 | 44.4 |
| 32 | 0.25 | 1.0 10$^{11}$ | 6.1 | 4.3 | 1.53 | 36.7 |
| 36 | 0.25 | 8.2 10$^{10}$ | 7.0 | 4.0 | 1.75 | 42.0 |
| 40 | 0.26 | 7.1 10$^{10}$ | 7.0 | 3.8 | 1.82 | 43.7 |

Effect of Nitrate Concentration

Specific growth rate was very similar when nitrate concentration in the medium was enhanced from 10 to 40 mM, as can be observed in Table 6. However, maximum volumetric lutein content in the exponential phase increased significantly (40%) when nitrate concentration in the medium was raised from 10 to 30 mM, keeping constant at 40 mM and the maximal lutein content at the end of the culture increased three times when nitrate concentration was raised from 10 to 40 mM. Moreover, lutein productivity was enhanced by about 50%, as nitrate concentration in the medium was increased from 10 to 40mM.

TABLE 6

Effect of nitrate concentration

| Nitrate | µ | MCD | MLEP | MLC [mg | Lutein Production | |
|---|---|---|---|---|---|---|
| [mM] | [h$^{-1}$] | [cells$^{-1}$] | mg l$^{-1}$] | g$^{-1}$DW] | mg l$^{-1}$h$^{-1}$ | mg l$^{-1}$d$^{-1}$ |
| 10 | 0.34 | 5.0 10$^{10}$ | 5.7 | 3.3 | 1.94 | 46.6 |
| 20 | 0.34 | 5.0 10$^{10}$ | 6.0 | 3.3 | 2.04 | 49.0 |
| 30 | 0.35 | 6.0 10$^{10}$ | 8.0 | 3.9 | 2.80 | 67.2 |
| 40 | 0.36 | 6.5 10$^{10}$ | 8.0 | 4.2 | 2.88 | 69.1 |

Effect of Acetate Concentration

The effect of acetate (mixotrophic growth) on cell growth, lutein content and lutein productivity is shown in Table 7. Specific growth rate increased from 0.46 to 0.55 h$^{-1}$ when the acetate in the medium was increased from 0 to 20 mM, keeping constant at higher acetate concentrations up to 60 mM. Maximum volumetric lutein content in the exponential phase was doubled from 5.5 to 11 mg l$^{-1}$ as the acetate in the medium was raised from 0 to 40 mM, keeping this value thereafter. With regard to lutein productivity, it was enhanced 2.4 times, reaching values of 145.2 mg l$^{-1}$day$^{-1}$, when the acetate concentration in the medium was increased from 0 to 40 mM, not increasing at higher concentrations of acetate.

TABLE 7

Effect of acetate concentration

| Acetate | µ | MCD | MLEP | MLC | Lutein Production | |
|---|---|---|---|---|---|---|
| [mM] | [h$^{-1}$] | [cells$^{-1}$] | [mg l$^{-1}$] | [mg g$^{-1}$DW] | mg l$^{-1}$h$^{-1}$ | mg l$^{-1}$d$^{-1}$ |
| 0 | 0.46 | 1.1 10$^{11}$ | 5.5 | 3.8 | 2.53 | 60.7 |
| 20 | 0.55 | 1.3 10$^{11}$ | 8.7 | 5.0 | 4.78 | 114.7 |
| 30 | 0.54 | 1.2 10$^{11}$ | 9.7 | 5.1 | 5.23 | 125.5 |
| 40 | 0.55 | 1.4 10$^{11}$ | 11.0 | 5.2 | 6.05 | 145.2 |
| 50 | 0.55 | 1.2 10$^{11}$ | 10.5 | 4.6 | 5.77 | 138.5 |
| 60 | 0.52 | 1.3 10$^{11}$ | 11.0 | 4.8 | 5.72 | 137.3 |

Combined Effects of Acetate Concentration and Light Irradiance

The combined effect of acetate concentration and light irradiance on growth, lutein content and lutein productivity has been also studied in Chlorella sorokiniana, as can be observed in Table 8. The specific growth rate and the maximum volumetric lutein content in the exponential phase only increased slightly when irradiance was raised from 460 to 690 µE m$^{-2}$s$^{-1}$, for both concentrations of acetate used in the experiment. Lutein production was around 30% higher in a medium containing 20 mM acetate when light irradiance was increased, from 460 to 690 µE m$^{-2}$s$^{-1}$. However, only a small effect of irradiance on productivity could be observed when the acetate in the medium was 30 mM.

TABLE 8

Effect of light irradiance and acetate concentration

| Acetate [mM] | Irradiance [µE m$^{-2}$s$^{-1}$] | µ [h$^{-1}$] | MCD [cells l$^{-1}$] | MLEP [mg l$^{-1}$] | MLC [mg g$^{-1}$DW] | Lutein Production mg l$^{-1}$h$^{-1}$ | mg l$^{-1}$d$^{-1}$ |
|---|---|---|---|---|---|---|---|
| 0  | 460 | 0.46 | 1.1 10$^{11}$ | 5.5  | 3.8 | 2.53 | 60.7  |
| 20 | 460 | 0.55 | 1.3 10$^{11}$ | 8.7  | 5.0 | 4.78 | 114.7 |
| 20 | 690 | 0.60 | 1.0 10$^{11}$ | 10.5 | 4.7 | 6.30 | 151.2 |
| 30 | 460 | 0.54 | 1.2 10$^{11}$ | 9.7  | 5.1 | 5.23 | 125.5 |
| 30 | 690 | 0.59 | 1.1 10$^{11}$ | 10.0 | 3.7 | 5.90 | 141.6 |

What we claim is:

1. A process of obtaining lutein from green algae, which process comprises:
    (a) cultivating a *Chlorella sorokiniana* (SAG 211-32) under cultivating conditions suitable for producing lutein in an amount that is at least about 90% by weight of the total carotenoids produced as a result of said cultivating step, the cultivating conditions comprising 20 to 60 mM salts of acetic acid and light irradiation of from about 200 to 1,500 µEm$^{-2}$s$^{-1}$;
    (b) harvesting the cultivated algae containing lutein; and
    (c) obtaining the lutein from the harvested algae containing lutein.

2. The process of claim 1 wherein the green algae is cultivated in a mixotrophic culture medium.

3. The process of claim 2 wherein the medium contains from about 20 to about 60 mM salts of acetic acid and from about 10 to about 60 mM of nitrates.

4. The process of claim 1 which further comprises adding an antioxidant at step (b) or step (c).

5. The process of claim 4 wherein the antioxidant is alpha tocopherol.

6. A process of obtaining at least one of lutein or a lutein-enriched product comprising:
    (a) cultivating cells of a strain of the green algae *Chlorella sorokiniana* (SAG 211-32) under conditions suitable for producing lutein in an amount that is at least about 90% by weight of total carotenoids produced as a result of said cultivating step, the cultivating conditions comprising 20 to 60 mM salts of acetic acid and light irradiation of from about 200 to 1,500 µEm$^{-2}$s$^{-1}$; and
    (b) harvesting the cells to form a concentrated suspension of algae cells.

7. The process of claim 6 further comprising:
    (c) disrupting the cells of the concentrated suspension; and
    (d) drying the disrupted cells to obtain at least one of lutein or a lutein-enriched product.

8. The process of claim 6 wherein an antioxidant and an emulsifier are added to the suspension of step (b).

9. The process of claim 6 wherein the algae is cultivated in a mixotrophic culture medium.

10. The process of claim 9 wherein the medium contains from about 20 to about 60 mM salts of acetic acid and from about 10 to about 60 mM of nitrates.

11. The process of claim 1 or 6 wherein the algae is cultivated at a temperature of from about 20 to about 40° C.

12. The process of claim 1 or 6 wherein the cultivation is conducted under stress conditions selected from the group consisting of light irradiation, chemical stress, salts, pH, temperature and oxidative stress.

13. The process of claim 1 or 6 wherein the cultivation is conducted in a photo-bioreactor.

14. A dried *Chlorella sorokiniana* (SAG 211-32) product obtained by the process of claim 7, wherein lutein comprises at least about 90% by weight of total carotenoids in the product, and the product has a lutein/zeaxanthin ratio of greater than about 5 and a chlorophyll A/lutein ratio of less than about 10.

\* \* \* \* \*